United States Patent [19]

Digby

[11] 4,173,230

[45] Nov. 6, 1979

[54] NOISE ELIMINATION AND REFRACTORY PERIOD CONTROL IN DEMAND PACERS

[75] Inventor: Dennis Digby, Brooklyn Park, Minn.

[73] Assignee: Biotronik Mess- und Therapiegeräte GmbH & Co., Berlin, Fed. Rep. of Germany

[21] Appl. No.: 917,129

[22] Filed: Jun. 19, 1978

[30] Foreign Application Priority Data

Aug. 19, 1977 [GB] United Kingdom ............... 34914/77

[51] Int. Cl.² .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,557,796 | 1/1971 | Keller, Jr. ..................... | 128/419 PG |
| 3,903,897 | 9/1975 | Woollows et al. ............ | 128/419 PG |
| 4,043,347 | 8/1977 | Renirie ........................... | 128/419 PG |
| 4,049,003 | 9/1977 | Walters ........................... | 128/419 PG |
| 4,049,004 | 9/1977 | Walters ........................... | 128/419 PG |

*Primary Examiner*—William E. Kamm
*Attorney, Agent, or Firm*—Spencer & Kaye

[57] ABSTRACT

Oscillator pulses are coupled to a counter, the ultimate count interval of which causes an output amplifier to produce a stimulating pulse and also to reset itself. A refractory control flip-flop is also thereby reset, and blocks demand mode resetting pulses for the refractory period. A second counter is resettable by the input amplifier, and defines a count interval during which noise pulses are rejected. A second flip-flop is responsive to the second counter and to the refractory flip-flop selectively to reset the first counter based on demand pacing criteria.

3 Claims, 2 Drawing Figures

NOISE ELIMINATION AND REFRACTORY PERIOD CONTROL IN DEMAND PACERS

TECHNICAL FIELD

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may or may not be implanted in the body, are well-known. Pacemakers can be classified into demand and non-demand types. A demand pacemaker only issues an artificial pulse if the heart does not produce its own satisfactory natural beat, whereas a non-demand pacemaker issues artificial stimulating pulses without regard to the presence or absence of a natural beat.

A demand pacemaker normally includes an input amplifier for receiving and amplifying electrical signals from the heart (which signals might result from either a natural beat or an artificial pulse which has just been generated by the pacemaker), a pacemaker control circuitry which receives the amplified signals and which causes a new artificial stimulating pulse to be generated (for transmission to the heart) only if the amplified signals, or lack thereof, show that an artificial stimulating pulse is required by the heart (i.e. on demand), and an output amplifier which receives and amplifies the artificial pulses generated by the control circuitry, for passage to the heart.

Many types of pacemaker control circuitry as described above are available. Some function on an analog basis to produce the accurately-timed artificial stimulating pulses, whereas several recent designs employ digital circuitry.

With demand pacemakers, it is highly desirable to provide protection for the input circuitry from noise. Should a person bearing an implanted demand pacemaker meet an environment of high electrical noise, this noise may be picked up by the input amplifier which may then be incapable of distinguishing the picked-up signals from the signals it normally receives from the heart. In such circumstances, the circuitry is likely to consider the noise signals in the same manner as if it had received signals arising from a natural heart beat—it will operate in its usual demand mode by not issuing artificial stimulating pulses to the heart. Since the heart may not be operating normally, and may indeed require artificial stimulation, these noise signals preventing such stimulation can lead to a dangerous condition for the person concerned.

Noise protection circuits have been incorporated into demand pacemakers in the past. For example, several include filters to attenuate noise signals of particular frequencies (particularly the commercial power mains frequency).

DISCLOSURE OF INVENTION

We have now developed a novel noise detection circuit for use in protecting demand pacemakers and which can be effciently constructed with a small number of components of digital function. This is particularly useful in that it enables the components to be included in an integrated pacemaker circuit, e.g. of MSI or LSI construction.

According to the invention there is provided an implantable, body tissue stimulating apparatus comprising means for providing electrical signals for artificially stimulating body tissue upon demand, said providing means including an input amplifier for receiving input signals from the body for controlling the demand status of the apparatus, means responsive to signals from the input amplifier for distinguishing whether one or more input signals are received by said input amplifier within a predetermined period of time, and demand status control means responsive to said distinguishing means for enabling the providing means to function in its demand mode if only one signal is received within said predetermined period of time and for causing the providing means to function in a non-demand mode if more than one input signal is received within said predetermined period of time.

BRIEF DESCRIPTION OF THE DRAWINGS

Preferred features of the invention are illustrated in the accompanying drawings, in which.

BEST MODE OF CARRYING OUT THE INVENTION

Figure 1:
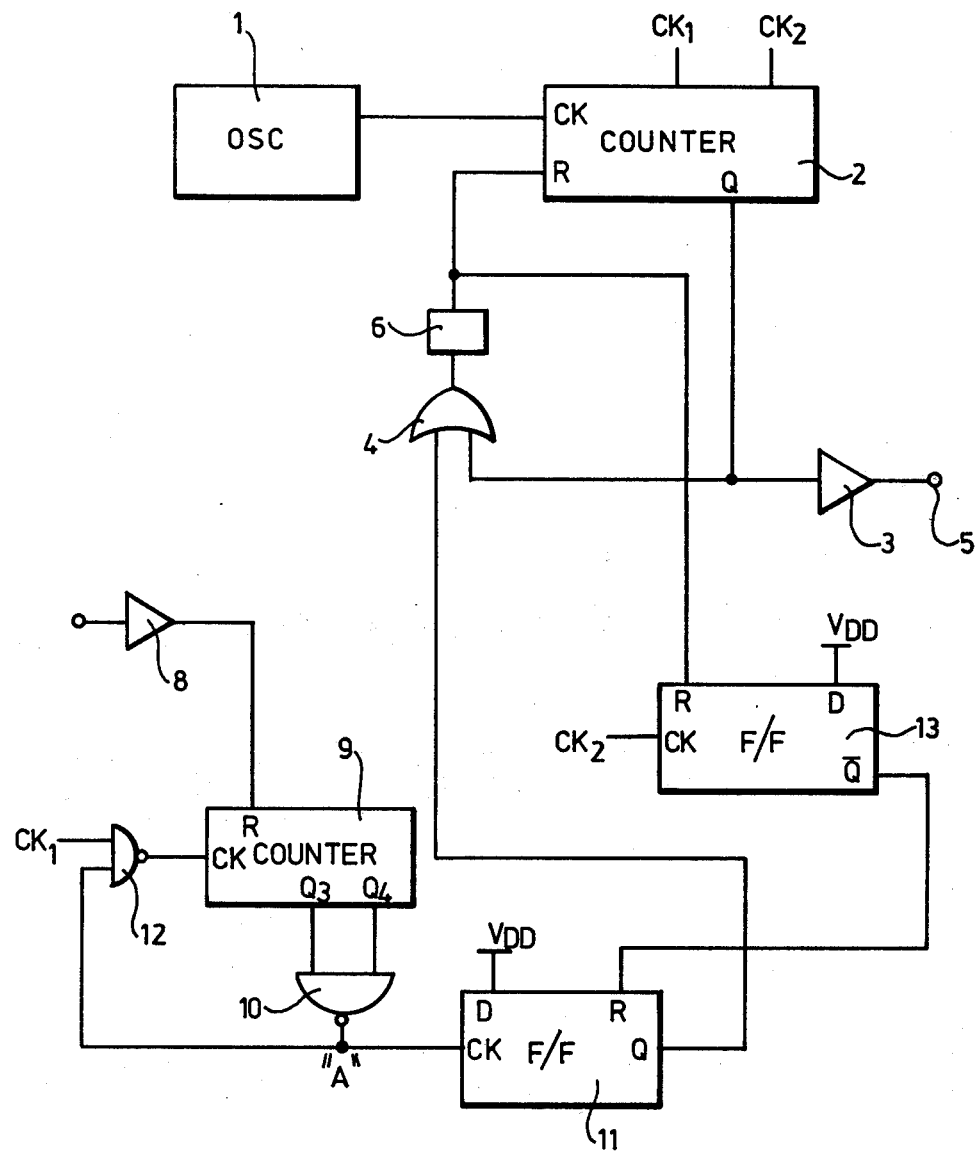
FIG. 1 shows a schematic electrical circuit diagram of an implantable, demand fixed-rate cardiac pacemaker according to the invention.

Referring to FIG. 1, the pacemaker comprises an oscillator 1 which clocks a ripple counter 2. A cardiac stimulating pulse rate is obtained from an appropriate output stage, Q, of counter 2 and is provided to an output amplifier 3 and to one input of an OR gate 4. The output amplifier 3 provides amplified tissue stimulating pulses to a connection 5 for coupling to an electrode leading to the heart. The output of OR gate 4 is supplied to a monostable 6, which is employed to reset counter 2.

The pacemaker also includes an input amplifier 8 which receives electrical signals generated at the heart (e.g. arising from natural heart beats) and supplies these signals, amplified, to the reset input of a ripple counter 9.

Two of the output stages of counter 8, nominated Q3 and Q4, provide inputs to a NAND gate 10, the output of which supplies the clock input to a D-type flip-flop 11 and an input to a NAND gate 12. The latter clocks ripple counter 9.

The Q output of flip-flop 11 supplies a second input to OR gate 4, and the D-input of flip-flop 11 is tied to the positive supply rail.

A further D-type flip-flop 13 is provided which is reset from the output of monostable 6 and whose $\overline{Q}$ output is employed to reset flip-flop 11. The D-input of flip-flop 13 is tied to the positive supply rail.

The counter 2 also supplies two clock outputs, $CK_1$ and $CK_2$. $CK_1$, having a period of 8 msecs, is employed to provide a second input to NAND gate 12, and $CK_2$ is employed to clock flip-flop 13. The clock pulse $CK_2$ arises 320 msecs after counter 2 is reset.

The pacemaker operates as follows. In its fixed rate mode, with neither noise nor natural heart beats being detected and amplified by input amplifier 8, counter 2 issues a continuous series of tissue stimulating pulses to output amplifier 3. The reset for counter 2 after each pulse occurs via OR gate 4, and monostable 6. The counter 2 is reset on the trailing edge of the monostable pulse and the firing time of the latter thus determines the pulse width of each stimulating pulse issued by counter 2.

Each reset pulse provided by monostable 6 also resets flip-flop 13, holding its $\overline{Q}$ output high. This reset holds until flip-flop 13 is clocked by a clock pulse $CK_2$. Until this clocking occurs, the $\overline{Q}$ output of flip-flop 13 holds a reset of flip-flop 11. The purpose of flip-flop 13 is to create a refractory period of 320 msecs—a period of time after a pacemaker pulse or a natural beat during which any input to the pacemaker via input amplifier 8 has no effect on the pacemaker behavior.

The purpose of counter 9, flip-flop 11 and associated circuitry is to allow a single pulse at the input amplifier 8 to reset counter 2 if the pulse occurs outside the refractory period. In such a circumstance, the pacemaker acts in a normal demand mode—only issuing pacemaker pulses if a natural beat is missing.

For explanation of the normal demand mode operation, assume initially that counter 2 has issued a pulse to cause itself to reset via OR gate 4. This reset will have reset flip-flop 13 and this, via the $\overline{Q}$ output of the latter, will also reset flip-flop 11. The Q output of flip-flop 11 will be low. Assume also that counter 9 is full, in the sense that the Q3, Q4 stages are high. This will cause point "A" to be low, and the output of NAND gate 12 to be high, thus locking out further $CK_1$ clock pulses to counter 9.

Counter 2 recommences counting and until the count $CK_2$ is reached, the reset on flip-flop 11 will be held. On reaching $CK_2$, flip-flop 13 clocks and its $\overline{Q}$ output goes low, removing the flip-flop 11 reset. This is the end of the refractory period. Since counter 9 is locked out, and point "A" is locked low, flip-flop 11 is not clocked and its Q output remains low.

If a single input pulse is received by amplifier 8 after the end of the refractory period (i.e. as a result of a natural heart beat), counter 9 is reset, Q3 and Q4 go low, and the point "A" goes high to clock flip-flop 11. The Q output of the latter resets counter 2 via OR gate 4 to inhibit the pacemaker pulse being generated, and recommences the refractory period by resetting flip-flop 13. Counter 9, in the meantime, commences counting clock pulses $CK_1$ and locks out again when Q3, Q4 go high. It is of no consequence if the reset to counter 2 initiated by a natural heart beat arrives just as an artificial pulse is generated, since the natural beat and the stimulating pulse will essentially coincide.

If a series of input pulses are received having an interpulse period less than 88 msecs, counter 9 is continuously reset and, apart from the initial reset on the first of these pulses, point "A" does not make the low to high transition necessary to clock flip-flop 11. When this occurs, flip-flop 11 is then incapable of continuously resetting counter 2 and the pacemaker reverts to the fixed rate mode described above. The effect of the noise detection circuitry is hence to cause the pacemaker to operate in its fixed rate, non-demand mode in the presence of noise (or heart generated signals) having a period less than 88 msec. This figure of 88 msec arises in that it is the minimum time required to fill counter 9 (i.e. Q3 and Q4 high) after a first input pulse is received via amplifier 8 to reset counter 9. The maximum time required to fill counter 9 is 96 msec. The spread of 88 to 96 msec (1 clock period) is due to the asynchronous nature of the incoming signal to amplifier 8 compared to the next occurrence of a $CK_1$ clock pulse.

If a single input pulse is received during the last 88–96 msec of the refractory period, this effectively acts to extend the refractory period by up to 96 msec maximum, to provide a "system refractory period" of 416 msec maximum. This "refractory period extension" may be beneficial to the pacemaker in that extraneous signals present towards the latter part of the refractory period are ignored (as being natural heart beats) and the chance of the pacemaker being inhibited by unwanted signals (e.g. a large T-wave from the heart) is reduced.

Figure 2:
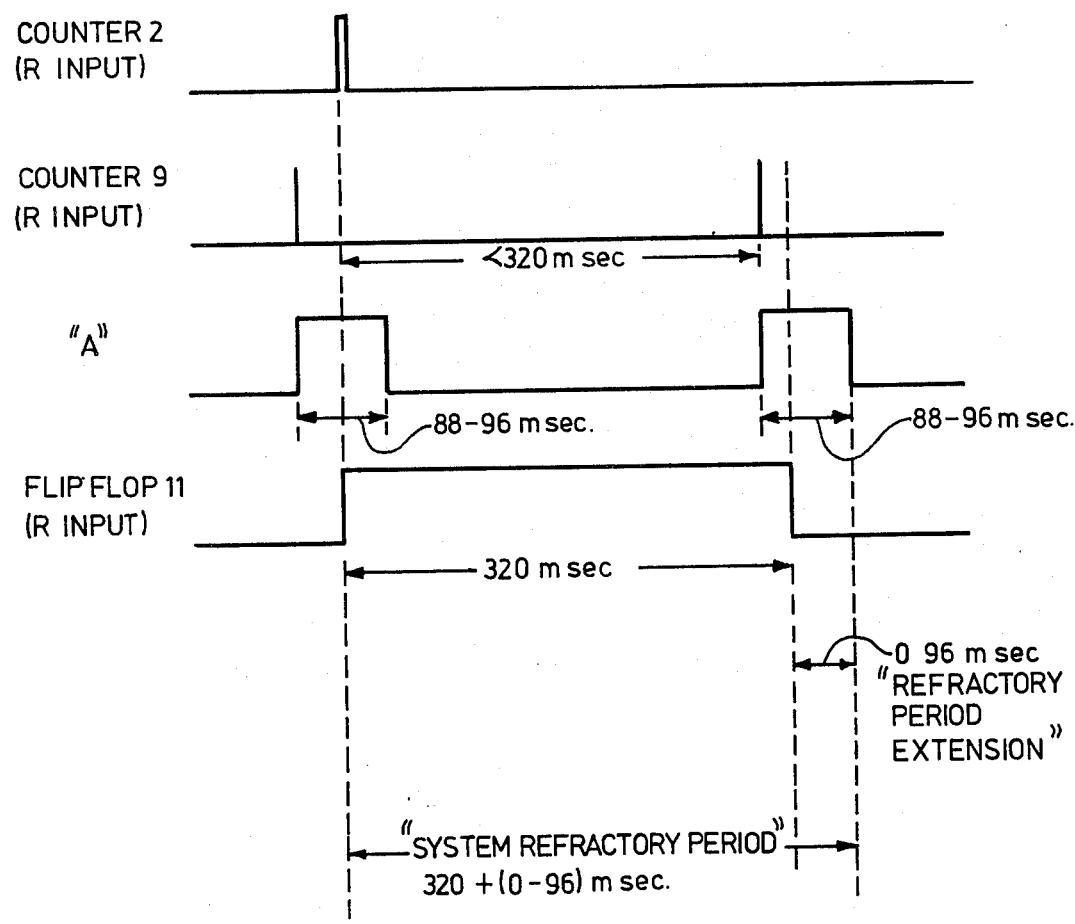
FIG. 2 is a timing diagram for use with FIG. 1.

This phenomenon of "refractory period extension" is best understood with reference to the timing diagram of FIG. 2. A reset to counter 9 arises towards the end of the refractory period and this sends the point "A" (clock input to flip-flop 11) high. The period for which "A" remains high after the refractory period of 320 msec expires (a maximum of 96 msecs) acts as a "refractory period extension" any input to amplifier 8 causing a reset on counter 9 during this extended period (the "system refractory period") will not inhibit the count being generated by the counter 2.

What is claimed is:

1. Demand cardiac stimulating apparatus comprising:
 (a) oscillator means;
 (b) first counter means, responsive to said oscillator means, for defining respectively larger predetermined first, second and third count intervals, said first counter being reset upon each achievement of said third count interval, and being resettable independently of said counts at any time completely to reinitiate its full counting sequence;
 (c) output amplifier means for generating a stimulating pulse upon each achievement by said first counter of said third count interval;
 (d) input amplifier means for sensing signals at the heart;
 (e) second counter means, controllably incremented upon each repetition by said first counter of said first count interval, said second counter means being reset to recommence counting by each signal sensed at the heart by said input amplifier means;
 (f) gating means, responsive to a predetermined terminal count of said second counter, for establishing a logic control state, said control state inhibiting further incrementing of said second counter until the next subsequent resetting of said second counter by said input amplifier;
 (g) first control means, responsive to first achievement by said first counter, after resetting thereof, of said second count interval, said first control means establishing a refractory period for said stimulating apparatus after each resetting of said first counter and otherwise independently of the state of said second counter; and
 (h) second control means inhibited by said first control means during said refractory period and thereafter being energized by termination of said logic control state, for resetting said first counter and thereby conditionally extending said refractory period as a function of said terminal count, also providing rejection of demand stimulating response to sensed signals having periodicity of less than said terminal count.

2. Apparatus as described in claim 1 wherein said first control means comprises a D-type flip-flop having its D-input maintained at a logic 1 state, its reset input connected to the reset input of said first counter, its clock input controlled by said second count interval of said first counter, and its $\overline{Q}$ output providing control for said second control means.

3. Apparatus as described in claim 2 wherein the second control means comprises a D-type flip-flop having its D-input maintained at a logic 1 state, its reset input coupled to said $\overline{Q}$ output of said first control means, its clock input controlled by said gating means, and its Q output coupled to reset said first counter.

* * * * *